United States Patent [19]
Miller

[11] Patent Number: 6,163,738
[45] Date of Patent: Dec. 19, 2000

[54] POINT OF PURCHASE GASOLINE ANALYZING/BLENDING

[75] Inventor: Charles B. Miller, Ashland, Ky.

[73] Assignee: Marathon-Ashland Petroleum, LLC, Findlay, Ohio

[21] Appl. No.: 07/708,585

[22] Filed: May 31, 1991

[51] Int. Cl.[7] .................................................. G06F 17/00
[52] U.S. Cl. .................. 700/239; 700/240; 700/242; 222/71; 222/132
[58] Field of Search ................................ 222/14, 16, 26, 222/28, 71, 132, 145; 700/231, 239, 240, 242

[56] References Cited

U.S. PATENT DOCUMENTS

| | | | |
|---|---|---|---|
| 2,722,826 | 11/1955 | Milligan | 73/53 |
| 3,385,680 | 5/1968 | Feld | 44/2 |
| 3,582,281 | 6/1971 | Fenske | 23/230 |
| 3,847,302 | 11/1974 | Krone et al. | 222/14 |
| 3,895,738 | 7/1975 | Buchanan | 222/26 |
| 4,479,807 | 10/1984 | Rebandt | 44/56 |
| 4,615,362 | 10/1986 | Hartman | 141/86 |
| 4,821,697 | 4/1989 | McDougal | 123/425 |
| 4,876,653 | 10/1989 | McSpadden | 364/479 |
| 4,951,720 | 8/1990 | Grantham | 141/44 |
| 4,963,745 | 10/1990 | Maggard | 250/343 |
| 4,974,552 | 12/1990 | Sickafus | 123/1 A |
| 4,978,029 | 12/1990 | Furrow | 222/1 |
| 5,018,645 | 5/1991 | Zinsmeyer | 222/14 |
| 5,029,100 | 7/1991 | Young et al. | 364/479 |
| 5,163,586 | 11/1992 | Zinsmeyer | 222/14 |

FOREIGN PATENT DOCUMENTS 2136118  9/1984  United Kingdom .

OTHER PUBLICATIONS

Precision Scientific, Bulletin 44770 AW–8, Chicago, IL, "Reid Monitor—Catalog 44770".
Oil & Gas Journal, Apr. 9, 1990, p. 43 "Reformulated Gasoline Will Challenge Product—Quality Maintenance".
Oil & Gas Journal, Apr. 23, 1990, p. 91, "Options to Meet 1990s Fuel Composition Rules Limited".
Legal Times, Jul. 23, 1990, "National Tank Truck Carrier, Inc., v. Environmental Protection Agency".
Hydrocarbon Processing, Mar. 1991, pp. 197–198, "Precision Reid Vapor Pressure Apparatus delivers fast, reliable results automatically".

*Primary Examiner*—Paul P. Gordon
*Attorney, Agent, or Firm*—Richard D. Stone

[57] ABSTRACT

Two, preferably three or more gasoline (or other fuel) blending components are delivered to a point adjacently point of sale to the motorist and are blended by an apparatus which proportions the flow of individual components in response to signals indicative of the gasoline quality variables, octane, Reid vapor pressure, percent alcohol, etc. (The preferred octane for control purposes is motor octane, but pump octane or research octane or any combination of these three may be utilized.)

1 Claim, 1 Drawing Sheet

POINT OF PURCHASE GASOLINE ANALYZING/BLENDING

BACKGROUND OF THE INVENTION

I. Field of the Invention

The present invention relates to the analysis and blending of motor vehicle fuels, generally classified in U.S. Patent and Trademark Office Class 250, Subclasses 243, 241, and 339.

II. Description of the Prior Art

The need for tailoring motor vehicle fuels, especially gasoline octane, to the needs of various consumer vehicles has long been apparent, and solutions have included providing a number of different gasoline pumps at a single retail outlet so that the consumer may select the pump which dispenses the fuel closest suited to his vehicle's requirements; and elaborate blending pumps which blend a very high octane component such as alkylate with a low octane gasoline according to an octane dialed into the dispensing pump. Recently, this situation has been complicated by mandated gasoline proposals before the Congress and various states, and by different tax treatments granted to ethanol, methanol, and other replenishable fuel components in different states. Also, legislation in specifying maximum Reid vapor pressure (RVP) in various locals has become popular and must be balanced against the need for some minimum RVP in order to ensure starting of the motor vehicle in cold weather and cold climates. Taken altogether, these motorist demands and government regulations can be satisfied only by blending gasoline from more than two components and by blending as close to the point of sale as possible.

Recent advances in octane determination include U.S. Pat. No. 4,800,279 to Hieftje et al.; U.S. Pat. No. 4,963,745 to S. M. Maggard; J. J. Kelley et al., 61 Analytical Chemistry 313–320, Feb. 15, 1989; and European Patent Office document 285,251 of October 1988. Reid vapor pressure can be analyzed intermittently or continuously by Reid Monitor No. 44770 by Precision Scientific Inc., Chicago.

SUMMARY OF THE INVENTION

I. General Statement of the Invention

According to the invention, two, preferably three or more gasoline (or other fuel) blending components are delivered to a point adjacent point of sale to the motorist and are blended by an apparatus which proportions the flow of individual components in response to signals indicative of the gasoline quality variables, octane, Reid vapor pressure, percent alcohol, etc. (The preferred octane for control purposes is motor octane, but pump octane or research octane or any combination of these three may be utilized.) Analysis of octane is preferably performed by near-infrared spectroscopy, more preferably NIR operating in the t-butyl/methyne band, and most preferably through a signal which comprises the second derivative of the absorbance in that particular band. Preferred methods of control are proportioning pumps operating in response to an octane or other variable, input by the consumer, and periodically or continuously reset according to feedback received from the octane measured in the blended fuel. Reid vapor pressure and other gasoline variables are controlled similarly. Setting of the variable speed proportioning pumps in response to information input by the consumer, processing of the NIR absorbance signal, and other quality control-indicative signals for feedback to the proportioning pumps, pricing and calculation of total cost are all well within the state of the art of computer technology.

II. Utility of the Invention

While the invention will be particularly preferred for use in gasoline dispensing pumps, it may be used for other fuels such as control of cetane in diesel fuel, nitrobenzene, and other alcohol fuels used for automobile racing and even liquified petroleum gases such as blending butane and propane for fuel and heating purposes.

APPARATUS

Figure 1:
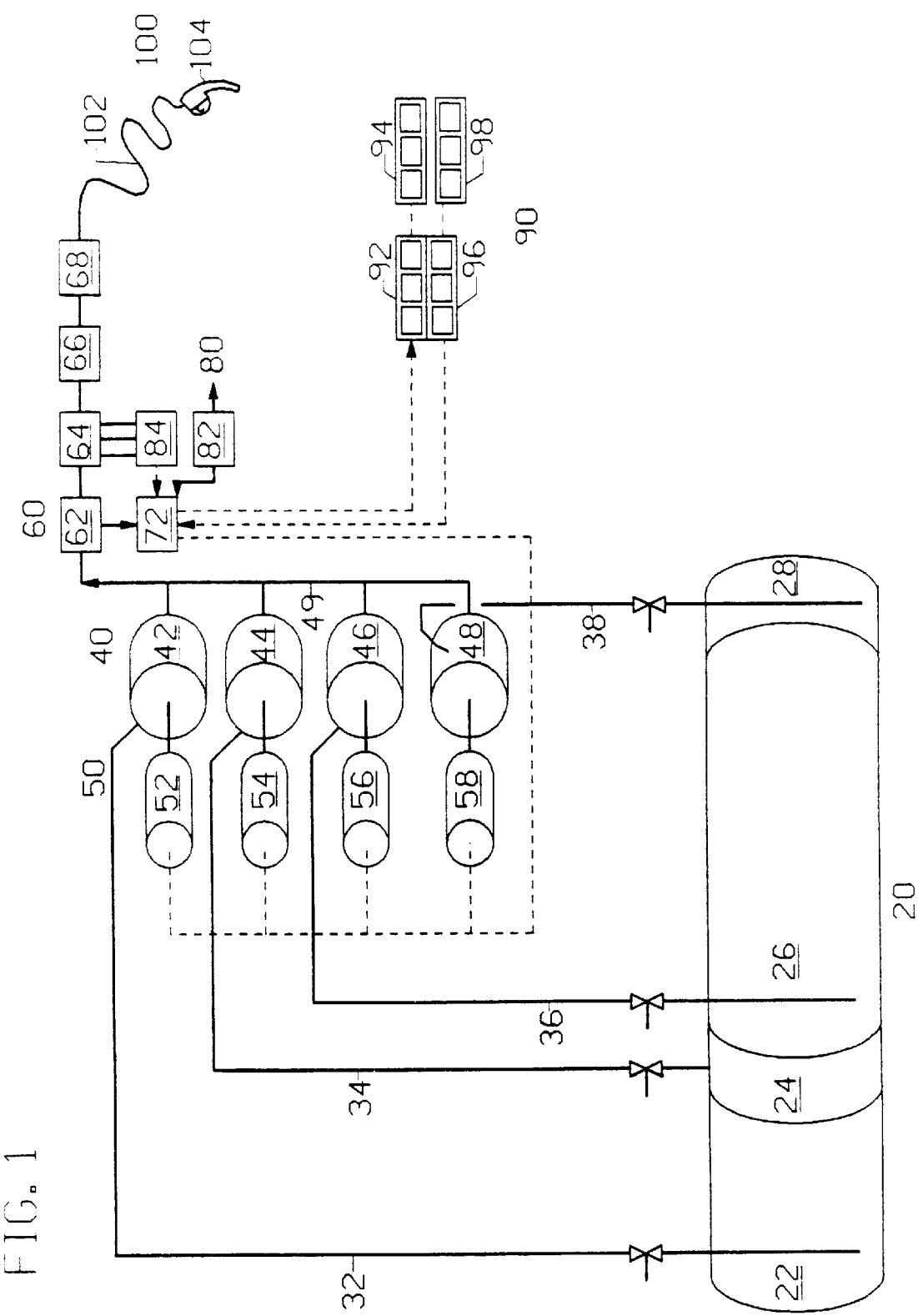
FIG. 1 shows schematically a preferred embodiment of the invention including principal components multiple fuel component storage means 20, individual conduit means 30, metering means 40, pump activating means 50, analyzing means 60, computer means 70, computer input means 80, computer display means 90, and fuel dispensing means 100.

The apparatus for use with the present invention is not narrowly critical and will be generally obtainable from commercial sources. Preferred devices for use with each of the principle components of the invention are:

Multiple Fuel Component Storage Means 20

The multiple fuel component storage means 20 can be any suitable, multiple storage means for receiving and dispensing the individual fuel components and may be located underground (with suitable leak retention means), above ground or transportable as in a tank truck. Reinforced fiberglass will be particularly preferred, but steel and other plastics can be used so long as they are proof against the components being contained. The compartments may be pressurized, e.g. with nitrogen to aid withdrawal.

While the particularly preferred embodiment having multiple compartments within a single tank is shown in FIG. 1, separate tanks may, of course, be employed for each component.

Individual Conduit Means 30

The individual conduit means 30 can be copper or suitable plastic tubing and should be equipped with hand valves, reverse-flow check valves, and suitable inlets for receiving the components; tank truck, rail car, barge, or other transport devices which may itself be compartmented so as to carry a number of different blending components.

Metering Means 40

The metering means 40 are preferably positive displacement pumps, e.g., gear pumps, piston pumps, peristaltic pumps, sliding vane pumps, or other positive displacement pumps which dispense a predetermined amount of volume with each stroke or rotation. The pumps may be variable-displacement themselves, but will be preferably driven by pump activating means 50 which can be adjusted to deliver more or less of each component per second during dispensing.

Analyzing Means 60

The analyzing means 60 comprises an near-infrared (NIR) analyzer operating in the range preferred in U.S. Pat. No. 4,963,745 to S. M. Maggard. A Reid vapor pressure analyzer, preferably an ASTM-approved analyzer, and an alcohol analyzer preferably an NIR or GC. Multiple analyzers adapted for analyzing individual components or desired physical properties of the fuel may be provided.

Computer Means 70

The computer means 70 is preferably a MicroVax digital computer and will most preferably take the second derivative of the absorbance in the preferred band. The computer should also be capable of receiving price and octane inputs and resetting itself to provide the desired octane, calculate the final price, gallons, and other desired variables such as cash or credit, etc.

Computer Input Means 80

The computer input means 80 can comprise a dial, a series of push buttons, a conventional telephone keypad, for inputting the price, the octane, charge or credit card, etc.

Computer Display Means 90

The computer display means 90 can be any sort of Blinn tube, liquid-crystal display, cathode-ray tube or other form of register for displaying the preset octane, price, volume delivered, and total sale plus Reid vapor pressure or any other parameters desired to be displayed.

Fuel Dispensing Means 100

The fuel dispensing means 100 comprises a conventional, flexible hose, nozzle and dispensing valve, all available from gasoline retail outlet equipment suppliers. The nozzle may be keyed to deliver only when set to the fuel required by the vehicle, e.g. by a bar-code on the gas tank coupled with a bar-code reader on the nozzle.

DESCRIPTION OF THE PREFERRED EMBODIMENTS

Referring to FIG. 1, the multiple fuel component storage means 20 are connected to individual metering means 40 through individual conduit means 30 which are driven by their respective pump activating means 50 and respond to signals received from computer means 70 which in turn receives signals from analyzing means 60 and sends outputs to computer display means 90 and to pump activating means 50. The fuel is dispensed through fuel dispensing means 100.

In operation, regular gasoline flows from regular gasoline compartment 22 through individual conduit means 32 and is metered by gasoline pump 42 through NIR Analyzer 62, Reid vapor pressure analyzer 64, alcohol analyzer 66, and meter 68, and the blended fuel is dispensed through hose 102 and nozzle and dispensing valve 104. Alkylate flows similarly from alkylate compartment 24 through its own individual system as does Reid vapor pressure component flow from Reid vapor pressure compartment 26 and ethanol from ethanol compartment 28.

The components are blended in mixer 49 which preferably employs a powered mixer for thorough blending. The NIR Analyzer 62 and the Reid vapor pressure analyzer 64 send signals to computer which, in turn, outputs signals to change the speed of gasoline metering motor 52, alkylate metering motor 54, and ethanol metering motor 58, at short intervals. Computer 70 also varies the speed of Reid vapor pressure metering motor 56 and responds to signals received from Reid vapor pressure analyzer 64. Computer has, before the dispensing begins, been inputted with information from price input 82 and octane input pad 84. During and after dispensing, until the next sale commences, computer displays appropriate data on octane display 92, price display 94, gallon/liter delivered display 96, and total sale display 98.

The customer sees little of this complexity but instead merely inputs (by hand or through the bar-codes discussed above) his desired octane, Reid vapor pressure (if it is desired to have the customer input that information), and sees the appropriate price displayed. He then opens nozzle and dispensing valve 104 and receives fuel of the desired octane, etc., with the usual gallons/liters dispensed and total sale information being displayed continuously during the dispensing. Appropriate inputting of customer credit cards, account numbers, cash or credit indications, vehicle numbers, can readily be provided for.

The inputting can be simplified, e.g. by providing means for inputting merely the make, model, engine, and year of the vehicle so that the computer itself determines the optimum fuel mix.

MODIFICATIONS

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein.

Reference to documents made in the specification is intended to result in such patents or literature being expressly incorporated herein by reference, including any patents or other literature references cited within such documents.

What is claimed is:

1. A flexible apparatus for location at or near the point of sale for the dispensing of quantities of fuels of variable octane and/or other fuel quality parameters comprising in combination:

(a) multiple fuel component storage means 20 having at least three compartments respectively communicating through (b) individual conduit means 30 to (c) metering means 40 comprising variable-speed motors actuating said positive displacement pumps for each component in response to a feedback signal and to (d) mixer means 49 for producing a blended product comprising at least three of said fuel components (e) near infrared absorbance analyzer 62 measuring at least a portion of said blended product and providing a first signal to (f) computer means 70, which provides a feedback signal to said metering means 40

(g) Reid vapor pressure analyzer 64 measuring at least a portion of said blended product and providing a second signal to said computer means 70

(h) computer input means 80 having input means for user inputting of desired levels of octane or cetane and at least one other fuel parameter;

(i) computer display means 90 which displays fuel price after said user inputting, and before said dispensing of said fuel; and (j) fuel dispensing means 100 communicating with said mixer means.

* * * * *